(12) United States Patent
Lee et al.

(10) Patent No.: US 9,181,520 B2
(45) Date of Patent: Nov. 10, 2015

(54) PHOTOBIOREACTOR FOR MASS-CULTURING MARINE MICROALGAE USING SEMI-PERMEABLE MEMBRANE

(75) Inventors: Choul-Gyun Lee, Seoul (KR); Z-Hun Kim, Incheon (KR)

(73) Assignee: INHA-INDUSTRY PARTNERSHIP INSTITUTE, Incheon-Si (KR)

( * ) Notice: Subject to any disclaimer, the term of this patent is extended or adjusted under 35 U.S.C. 154(b) by 865 days.

(21) Appl. No.: 13/132,157

(22) PCT Filed: Sep. 9, 2009

(86) PCT No.: PCT/KR2009/005109
§ 371 (c)(1),
(2), (4) Date: Jun. 24, 2011

(87) PCT Pub. No.: WO2010/064780
PCT Pub. Date: Jun. 10, 2010

(65) Prior Publication Data
US 2011/0247262 A1 Oct. 13, 2011

(30) Foreign Application Priority Data

Dec. 8, 2008 (KR) .................. 10-2008-0121700

(51) Int. Cl.
*A01K 7/00* (2006.01)
*C12M 1/09* (2006.01)
*C12M 1/00* (2006.01)

(52) U.S. Cl.
CPC ............. *C12M 23/56* (2013.01); *C12M 21/02* (2013.01); *C12M 23/14* (2013.01)

(58) Field of Classification Search
CPC ......... A01G 7/00; A01H 13/00; C12M 21/02; C12M 1/002
USPC .......................................................... 47/1.4
See application file for complete search history.

(56) References Cited

U.S. PATENT DOCUMENTS 4,086,161 A * 4/1978 Burton ........................ 210/602
4,888,912 A * 12/1989 Murray ........................... 47/1.4
5,528,856 A * 6/1996 Smith et al. ................... 47/59 R
7,980,024 B2 * 7/2011 Berzin et al. .................... 47/1.4
8,304,232 B2 * 11/2012 Morgan et al. ............ 435/292.1
8,409,845 B2 * 4/2013 Trent et al. ................. 435/257.1

FOREIGN PATENT DOCUMENTS

| CN | 2225133 Y | 4/1996 |
|---|---|---|
| EP | 0181609 B1 | 2/1990 |
| EP | 0182313 B1 | 2/1990 |
| JP | 09-001181 | 1/1997 |
| JP | 10-118689 A | 5/1998 |
| JP | 2004-113003 | 4/2004 |
| JP | 2007-330215 A | 12/2007 |
| KR | 10-1989-0004698 B1 | 11/1989 |
| KR | 10-1990-0001386 B1 | 3/1990 |
| WO | 2008/134010 A2 | 11/2008 |

* cited by examiner

*Primary Examiner* — Monica Williams
(74) *Attorney, Agent, or Firm* — Stuart H. Mayer; Mayer & Williams PC

(57) ABSTRACT

Provided is a photobioreactor for mass-culturing marine microalgae using a semi-permeable membrane. The photobioreactor installed in a floating type on a water level or soaked at a predetermined depth from the water level to mass-culture isolated marine microalgae includes a culturing bag formed of the semi-permeable membrane through which enables seawater to exist, but prevents the marine microalgae from being penetrated, the culturing bag being configured to provide a three-dimensionally culturing space for accommodating the marine microalgae; and a floating unit connected to the culturing bag to dispose the culturing bag near the sea level, thereby exposing the culturing bag to sunlight. Since the photobioreactor for mass-culturing the marine microalgae using the semi-permeable membrane is provided, the photobioreactor may be manufactured at a low cost and free from the spatial restrictions, thereby enabling the expansion of the photobioreactor in both the horizontal and vertical directions.

16 Claims, 7 Drawing Sheets

PHOTOBIOREACTOR FOR MASS-CULTURING MARINE MICROALGAE USING SEMI-PERMEABLE MEMBRANE

CROSS-REFERENCE TO RELATED APPLICATION

This application claims priority to Korean Patent Application No. 10-2008-0121700 filed on Dec. 3, 2008 and all the benefits accruing therefrom under 35 U.S.C. §119, the contents of which are incorporated by reference in their entirety.

BACKGROUND

The present disclosure relates to a photobioreactor for mass-culturing marine microalgae.

In recent, there is a rising interest on photosynthesis microorganisms or microalgae due to functional diversity. Also, studies with respect to the photosynthesis microorganisms or microalgae are researched in various fields. The microalgae are being actively used in studies for reducing carbon dioxide which becomes an object of attention in recent years due to environment pollution such as global warming. In addition, the microalgae are being utilized for studies related to the production of bio-energy such as biodiesel, bio-ethanol, and hydrogen gas, which are in the spotlight as the continuous energy sources in preparation for the running out of fossil fuels.

However, it should be necessary to mass-culture the microalgae at a high concentration so that carbon dioxide is significantly removed in quantity using the microalgae and useful products such as the bio-energy are mass-produced. Thus, technologies related to construction of large-scale culturing equipment are necessarily required.

In a related art, a photobioreactor having various shapes and installed in an indoor space is used as the culturing equipment for culturing the microalgae. The photobioreactor is formed of glass such expensive pyrex which increases transmittance of light and is used for pasteurization or an application material thereof. Also, the photobioreactor includes an artificial lighting unit. Thus, more capital and technologies should be invested to manufacture the photobioreactor, and much costs for maintaining/repairing and operating the photobioreactor are required after the photobioreactor is manufactured. It does cost much to expand the scale of the photobioreactor, and also, the photobioreactor involves spatial restrictions because a wide space is required for the photobioreactor. Furthermore, culture media for culturing the microalgae should be supplied and periodically replaced. Also, excreta generated when the microalgae are grown and metabolites disturbing the growth of the marine microalgae should be removed. That is, there are limitations that manufacturing costs is increased and the spatial restrictions occur. In addition, the manpower, equipment and costs for managing and operating the photobioreactor are required.

Thus, when considering that it is very important to secure economic feasibility for commercial mass-culture firstly, it does cost much to manufacture and maintain/repair the photobioreactor when a scale of the photobioreactor is expanded. In addition, the culture of the microalgae using the related-art photobioreactor in which a wide space is required and operation costs related to an operation of a lighting unit, preparation of culture media, and replacement of the culture media are involved does not a realistically appropriate way, in which the economic feasibility should be considered, for commercially mass-culturing the microalgae even though the culture of the microalgae is adequate for small scale culture which is an object of study. However, although the photobioreactor is adequate for producing expensive products such as medical supplies, reagents, high-quality chemicals, and health food supplements, the photobioreactor is not the realistically appropriate way for commercial large scale culture of the inexpensive products such as bio-energy in which the economic feasibility is very important.

As described above, the limitation related to the costs and space may act as stumbling blocks by which it is difficult to utilize the microalgae to produce useful products including the bio-energy or remove carbon dioxide. Thus, the development of the culturing technologies which cheaply and easily mass-culture the microalgae is urgently needed.

SUMMARY

The present disclosure provides a photobioreactor for easily and economically mass-culturing marine microalgae using a semi-permeable membrane, which is manufactured at a low cost and free from the spatial restrictions, and also, significantly reduces manpower and costs required for operating the photobioreactor without producing, supplying, and replacing the culture media.

In accordance with an exemplary embodiment, a photobioreactor for mass-culturing marine microalgae using a semi-permeable membrane, which installed in a floating type on a water level or soaked at a predetermined depth from the water level to mass-culture isolated marine microalgae, includes: a culturing bag formed of the semi-permeable membrane through which enables seawater to exist, but prevents the marine microalgae from being penetrated, the culturing bag being configured to provide a three-dimensionally culturing space for accommodating the marine microalgae; and a floating unit connected to the culturing bag to dispose the culturing bag near the sea level, thereby exposing the culturing bag to sunlight.

The photobioreactor may further include a form maintaining frame disposed inside or outside the culturing bag to maintain a three-dimensional shape of the culturing bag.

The culturing bag and the floating unit may be connected to each other through at least one rope, which is adjustable in length, the culturing bag may further include a weight connected to a lower portion of the culturing bag, and the culturing bag may be adjusted in depth of seawater through the length adjustment of the rope and the weight.

The photobioreactor may further include a gas supply tube connected to a lower portion of the culturing bag; and a gas supply unit configured to supply external air into the culturing bag through the gas supply tube, wherein the marine microalgae may be uniformly distributed within the culturing bag due to mixing operations of bubbles.

The culturing bag may have one of an inverted cone shape, a flexible tune shape, and a bag shape, and the gas supply tube and the weight may be connected to an apex of the culturing bag.

The culturing bag may be filled with exhaust gas for supplying carbon dioxide or a waste organic matter for supplying a nitrogen source, and the exhaust gas or the water organic matters filled into the culturing bag may be stored in the culturing bag by the semi-permeable membrane, but be not discharged into the sea.

The culturing bag may have an upper portion having a vertical cylindrical shape and a lower portion having an inverted cone shape, and the gas supply tube and the weight may be connected to an apex of the lower portion having the inverted cone shape.

The culturing bag may be provided in plurality, and the plurality of culturing bags may be vertically arranged, and wherein photobioreactor may include at least one weight connected to one or more culturing bags comprising the lowermost culturing bag.

The photobioreactor may further include a fixing unit fixed to a sea bottom in a state where the fixing unit is connected to one of the floating unit, the culturing bag, and the weight to restrict a moving range of the photobioreactor.

The floating unit may have at least one pair of connection points spaced a predetermined distance from each other, the culturing bag may have a long length and a narrow width and connected to the pair of connection points through one rope connected to each of both ends of a length direction of the culturing bag, and the culturing bag may be freely overturned by movement of a wave or seawater.

The culturing bag may have a long cylindrical shape and is connected to the floating unit in a state where the culturing bag is laid in parallel to a water level.

The culturing bag may have a central portion having a cylindrical shape and a pair of cone-shaped portions on both ends of the central portion, and the rope may be connected to an apex of each of the cone-shaped portions.

The photobioreactor may further include a fixing unit fixed to a sea bottom in a state where the fixing unit is connected to the floating unit.

BRIEF DESCRIPTION OF THE DRAWINGS

Exemplary embodiments can be understood in more detail from the following description taken in conjunction with the accompanying drawings, in which.

DETAILED DESCRIPTION OF EMBODIMENTS

Hereinafter, specific embodiments will be described in detail with reference to the accompanying drawings.

Figure 1:
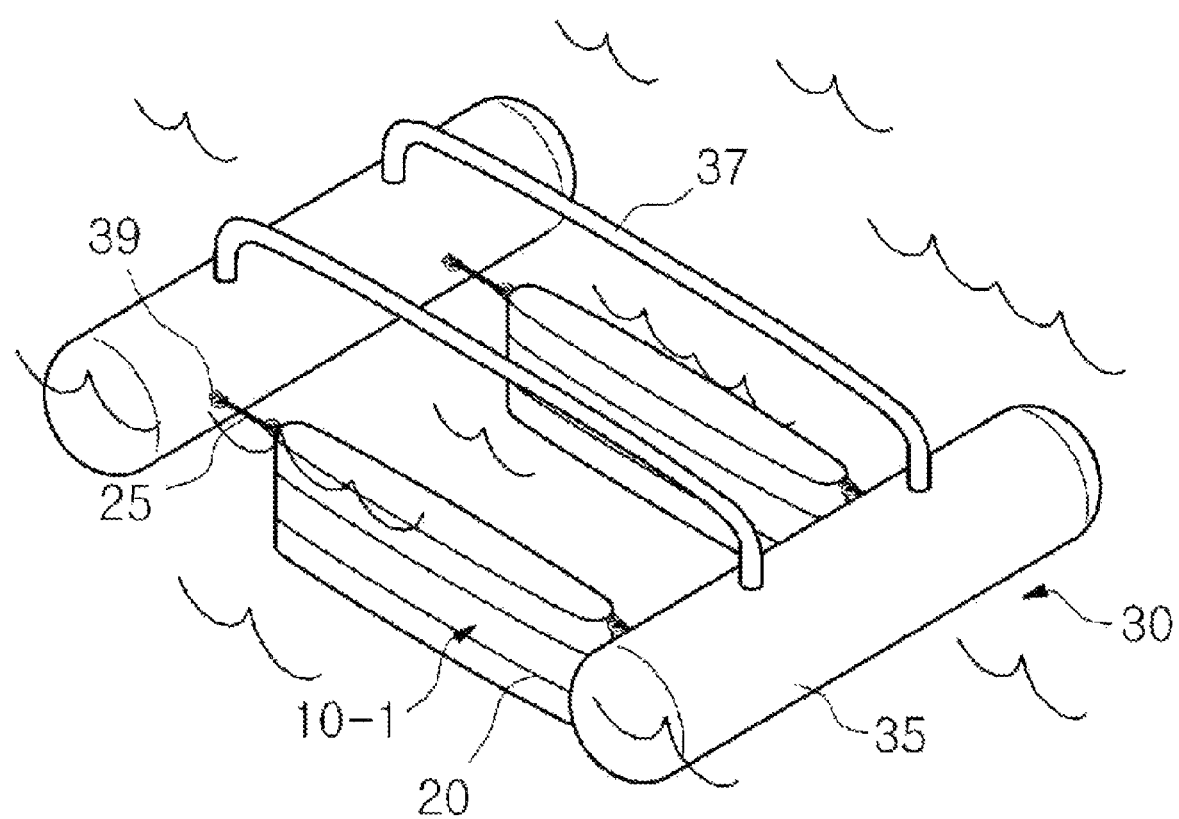
FIG. 1 is a schematic view of a photobioreactor in accordance with a first exemplary embodiment.

FIG. 1 is a schematic view of a photobioreactor in accordance with a first exemplary embodiment;

A photobioreactor for mass-culturing marine microalgae using a semi-permeable membrane in accordance with the first exemplary embodiment is installed in the sea to significantly overcome a spatial restriction due to its large scale. That is, a floating-type photobioreactor is installed on the sea to mass-culture marine microalgae while isolating the marine microalgae from each other.

Referring to FIG. 1, the photobioreactor in accordance with a first exemplary embodiment includes a culturing bag 10-1 and a floating unit 30 connected to the culturing bag 10-1 to dispose the culturing bag 10-1 near a water level, thereby exposing the culturing bag 10-1 to sunlight.

Particularly, the culturing bag 10-1 is made of a semi-permeable membrane which allows seawater to exit, but the marine microalgae to be blocked. Also, the culturing bag 10-1 is three-dimensionally formed to provide a culturing space for accumulating the marine microalgae. The culturing bag 10-1 further includes a form maintaining frame 20 which is disposed inside or outside the culturing bag 10-1 to maintain a three-dimensional shape of the culturing bag 10-1. Thus, the culturing bag 10-1 may be stably maintained in shape.

A main characteristic of the inventive concept is that the culturing bag 10-1 is manufactured using the semi-permeable membrane which allows the seawater to exit and allows the marine microalgae to be blocked. In detail, entering and exiting the seawater represents that nutrients dissolved in the seawater can be used as nourishment required for culturing the marine microalgae. Thus, it is unnecessary to supply separate culture media for culturing the marine microalgae. Also, excreta generated during growth of the marine microalgae and metabolites disturbing the growth of the marine microalgae may be dissolved in the seawater to remove the excreta and metabolites together with the seawater. Thus, it is unnecessary to perform a separate cleaning process for removing the excreta and the metabolites disturbing the growth of the marine microalgae. In addition, it is also unnecessary to replace the culture media. Furthermore, carbon dioxide dissolved in the seawater may be used for photosynthesis occurring while the growth of the marine microalgae. Also, the oxygen generated as a byproduct by the photosynthesis may pass through the semi-permeable membrane and discharged to the atmosphere. Also, blocking the marine microalgae represents that the marine microalgae can be cultured within only a manageable limited space. Thus, it may prevent marine pollution due to the mass propagation from occurring. In addition, the marine microalgae may be adequately cultured in number to easily harvest the cultured microalgae.

The floating unit 30 is a unit for locating the culturing bag 10-1 near the water level to expose the culturing bag 10-1 to the sunlight. As shown in FIG. 1, the floating unit 30 includes a pair of floating members 35 spaced from each other and a connection frame 37 connecting the floating members 35 to each other while maintaining a predetermined distance between the pair of floating members 35. However, the floating unit 30 is not limited to the above-described structure. For example, the floating unit 30 may be variously changed in size and shape according to those of the culturing bag 10-1.

Figure 2:
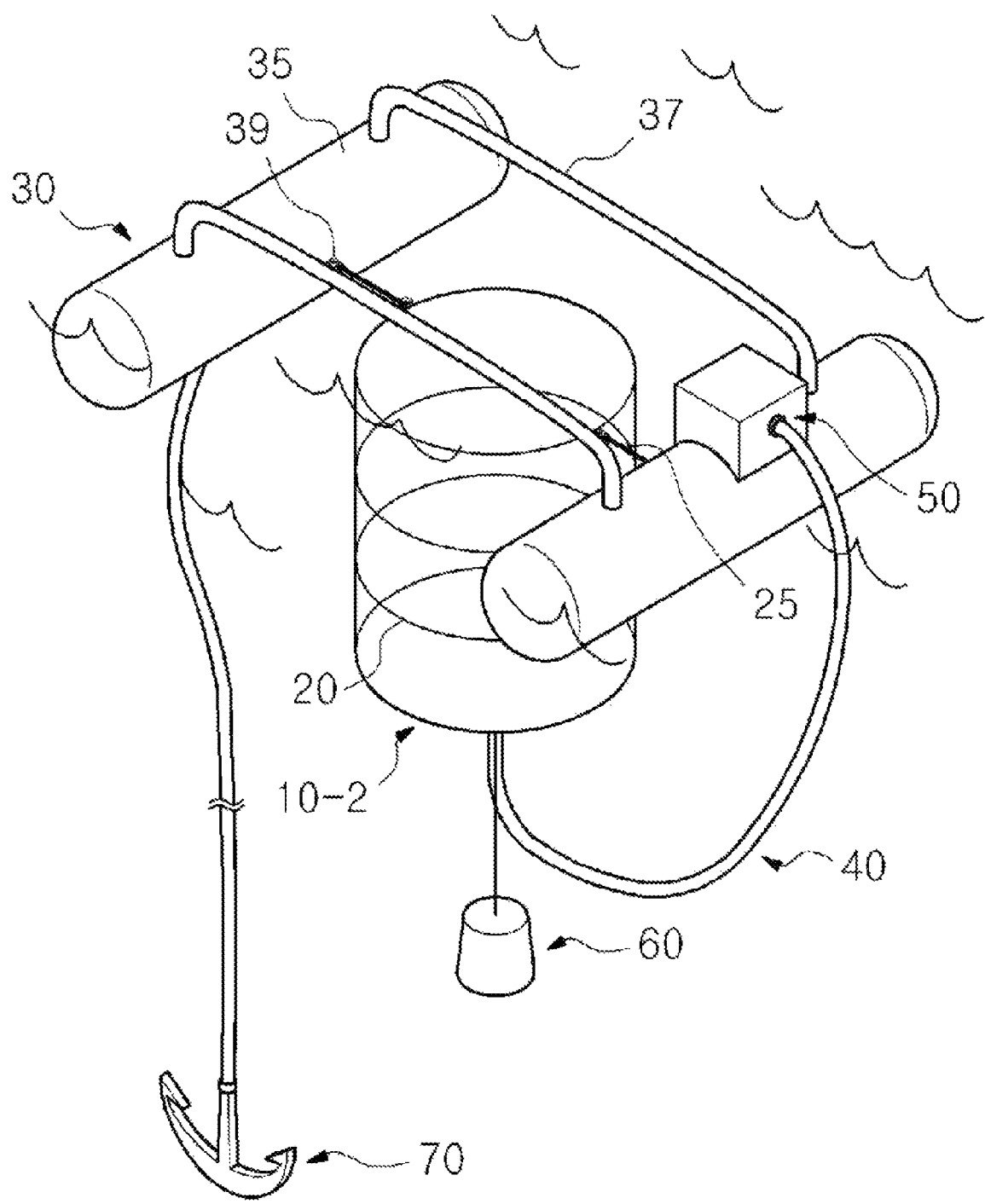
FIG. 2 is a schematic view of a photobioreactor in accordance with a second exemplary embodiment.

FIG. 2 is a schematic view of a photobioreactor in accordance with a second exemplary embodiment.

Referring to FIG. 2, like the first exemplary embodiment, a photobioreactor in accordance with a second exemplary embodiment includes a culturing bag 10-2 and a floating unit 30. The culturing bag 10-2 and the floating unit 30 are connected to each other through one rope 25, which is adjustable in length. The photobioreactor further include a weight 60 hung at a lower portion the culturing bag 10-2. Thus, the rope 25 may be adjusted in length and the culturing bag 10-2 is balanced by the weight 60 so that the culturing bag 10-2 is installed at a required depth of seawater.

A producible product may be varied according to a kind of marine microalgae to be cultured, and also, a required luminous intensity of sunlight may be changed according to a wavelength of the sunlight used for the photosynthesis and a kind of marine microalgae. Also, the transmitting sunlight may be changed in wavelength according to a depth of seawater. Thus, adjusting the depth of seawater at which the culturing bag 10-2 is installed represents that the culturing bag 10-2 is disposed at an adequate depth according to the kind of microalgae. That is, the culturing bag 10-2 may be disposed near the water level or in an underwater having a predetermined depth.

Also, the photobioreactor in accordance with the second exemplary embodiment further includes a fixing unit 70 fixed to a sea bottom in a state where it is connected to the floating unit 30 to restrict a movable range of the photobioreactor. As described above, the fixing unit 70 prevents the photobioreactor from being moved along movement of the seawater, thereby preventing the photobioreactor form getting out of a limited range. Thus, the fixing unit 70 may be formed of a material having a high specific gravity. For example, the fixing unit 70 may have a shape similar to an anchor which is easily fixed to the sea bottom.

Figure 3:
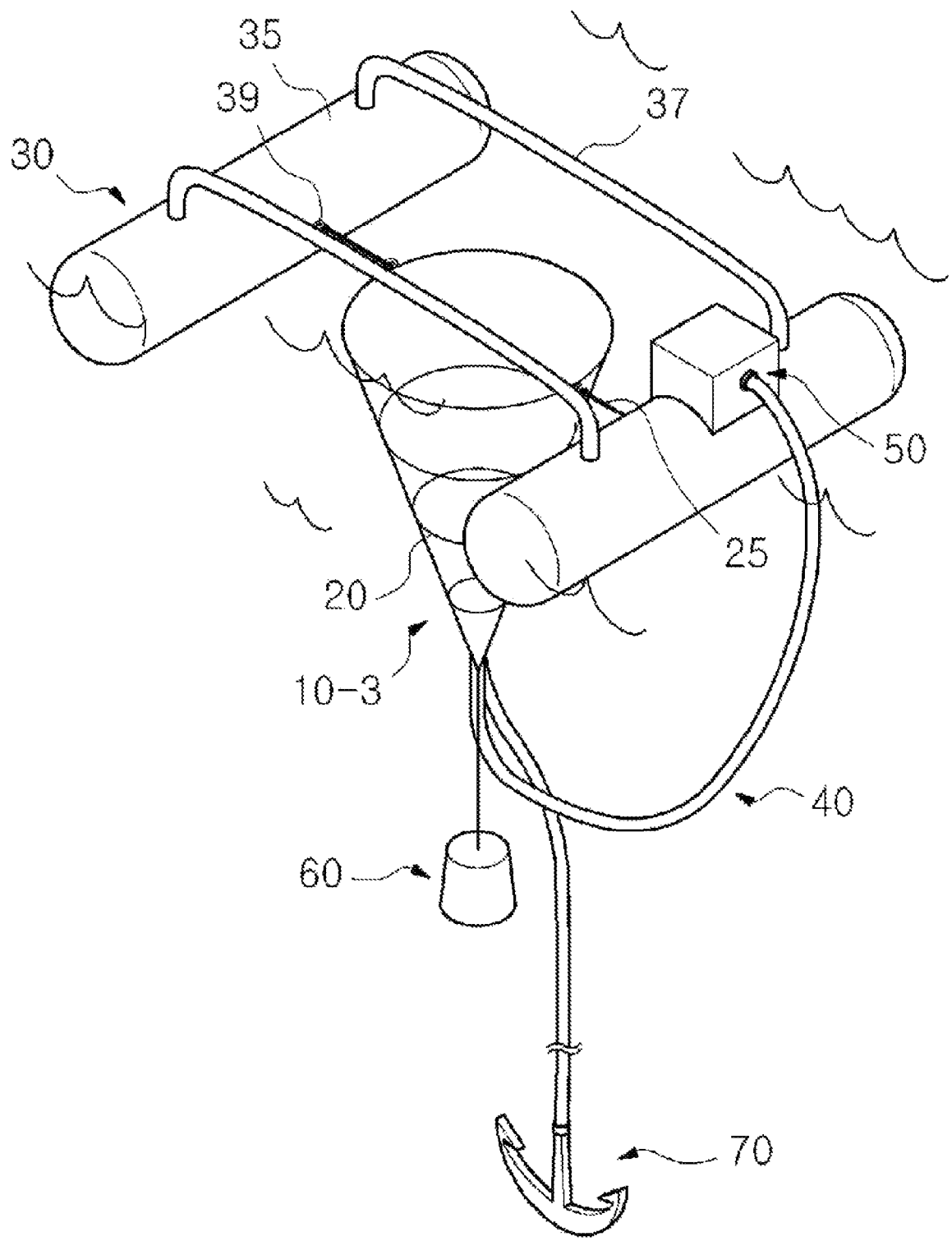
FIG. 3 is a schematic view of a photobioreactor in accordance with a third exemplary embodiment.

FIG. 3 is a schematic view of a photobioreactor in accordance with a third exemplary embodiment.

Referring to FIG. 3, a photobioreactor in accordance with a third exemplary embodiment includes a culturing bag 10-3 having an inverted cone shape and a floating unit 30. Also, like the second exemplary embodiment, the culturing bag 10-3 and the floating unit 30 are connected to each other through one or more ropes 25 which are adjustable in length. The photobioreactor further include a weight 60 hung at a lower portion the culturing bag 10-3.

Furthermore, the photobioreactor in accordance with the third exemplary embodiment further includes a gas supply tube 40 connected to a lower portion of the culturing bag 10-3 and a gas supply unit 50 supplying external air into the culturing bag 10-3 through the gas supply tube 40.

Thus, when a gas is supplied, marine microalgae may be uniformly distributed within the culturing bag 10-3 due to mixing operations of bubbles within the culturing space. Thus, culturing environments of the marine microalgae may be excellently maintained. Also, the marine microalgae may be naturally mixed within the culturing bag 10-3 by a flow of seawater due to a sea current and the ebb and flow of the tide. Thus, the gas supply may be selectively adopted as necessary when the mixing operation is further required.

In the photobioreactor in accordance with the third exemplary embodiment, the gas supply tub 40 and the weight 60 are connected to an apex of the culturing bag 10-3 having the inverted cone shape. Unlike the second exemplary embodiment, a fixing unit 70 is fixed to a sea bottom in a state where it 70 is connected to the apex of the culturing bag 10-3 to restrict a moving range of the photobioreactor.

Figure 4:
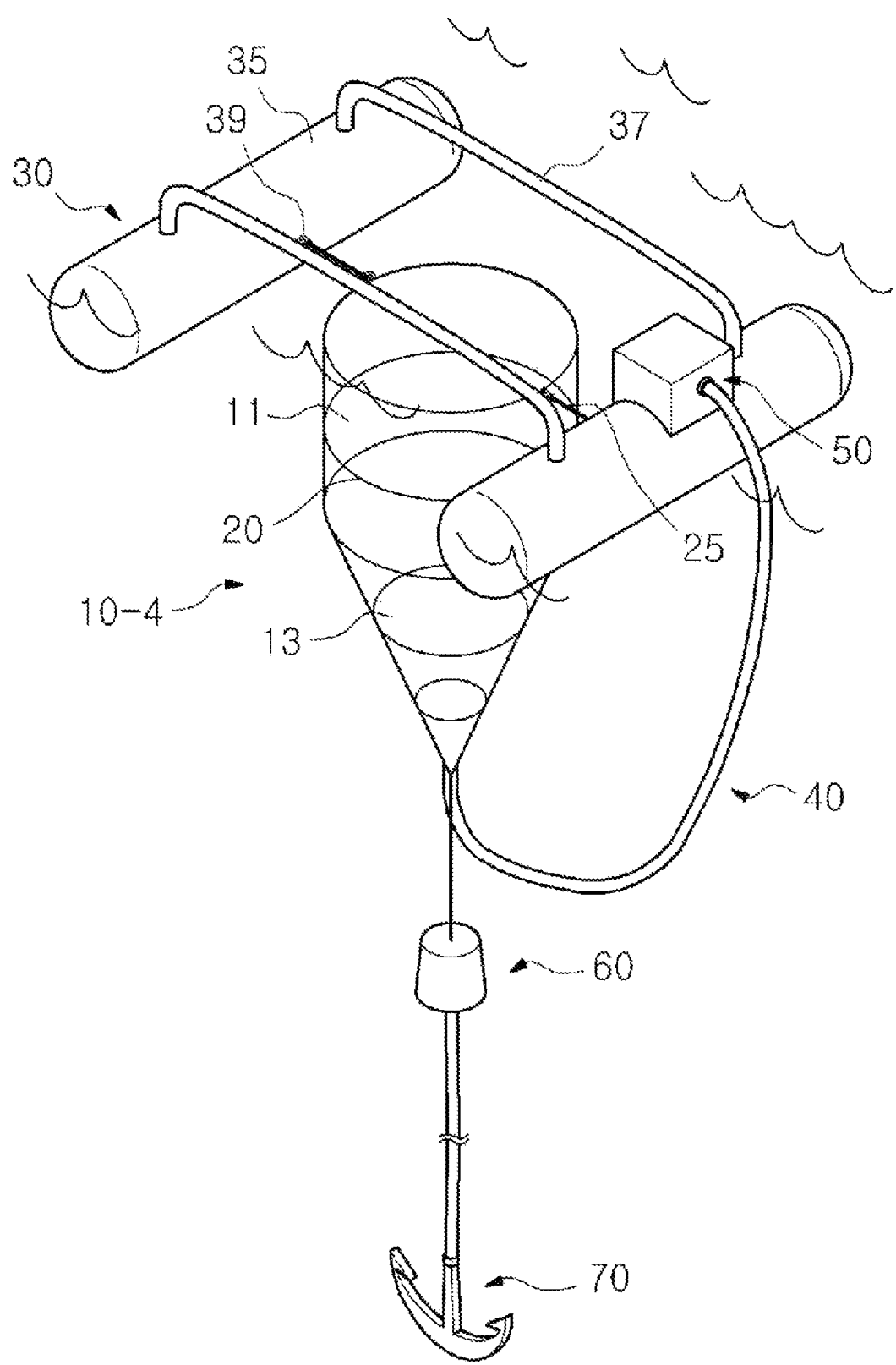
FIG. 4 is a schematic view of a photobioreactor in accordance with a fourth exemplary embodiment.

FIG. 4 is a schematic view of a photobioreactor in accordance with a fourth exemplary embodiment.

Referring to FIG. 4, a photobioreactor in accordance with a fourth exemplary embodiment includes an upper portion 11 having a vertical cylindrical shape and a culturing bag 10-4 including a lower portion 13 having an inverted cone shape. A gas supply tube 40 and a weight 60 are connected to an apex of the lower portion 13 having the inverted cone shape. However, unlike the second and third exemplary embodiments, the fixing unit 70 is fixed to a sea bottom in a state where it 70 is connected to the weight 60 to restrict a moving range of the photobioreactor.

Figure 5:
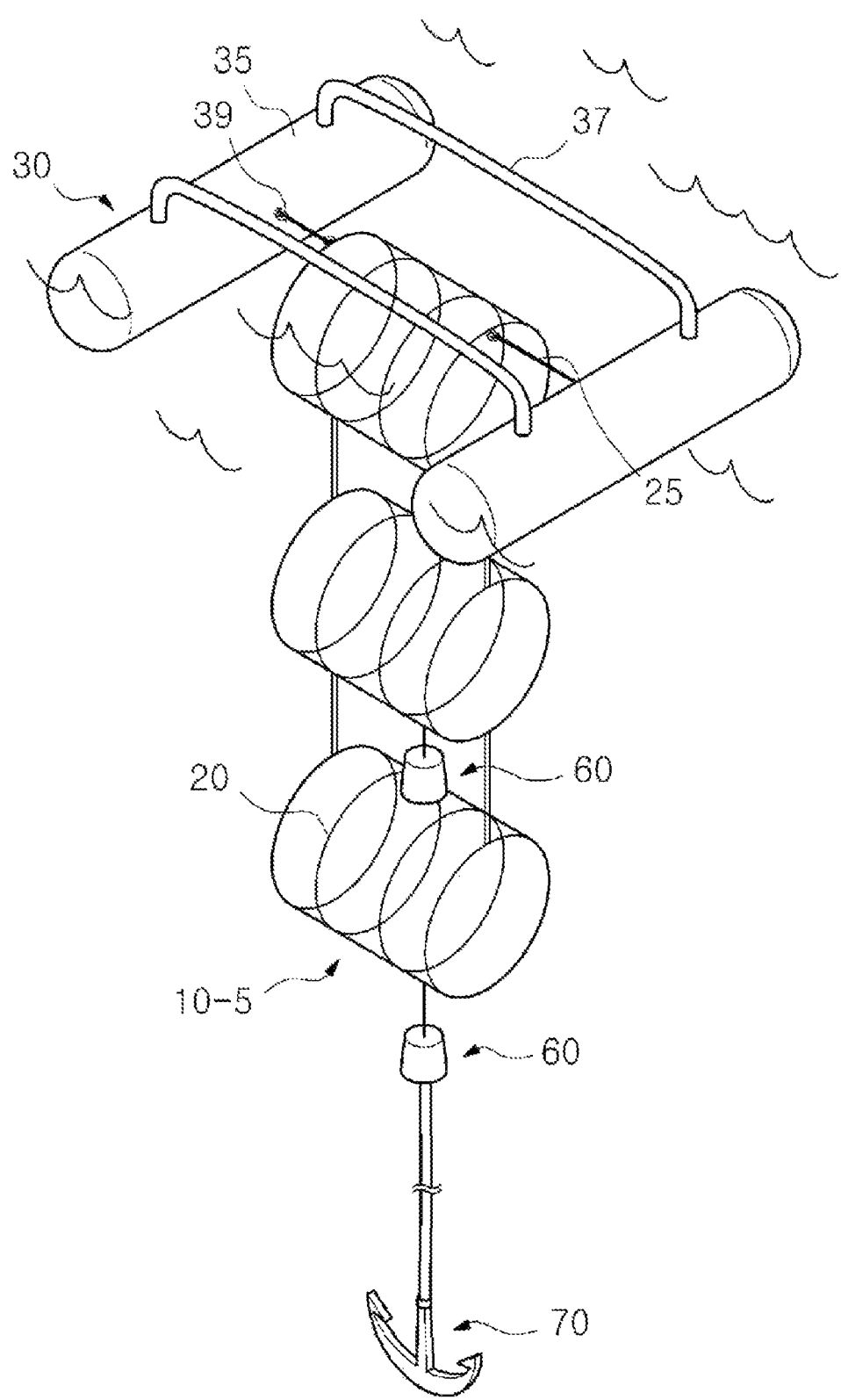
FIG. 5 is a schematic view of a photobioreactor in accordance with a fifth exemplary embodiment.

FIG. 5 is a schematic view of a photobioreactor in accordance with a fifth exemplary embodiment.

Referring to FIG. 5, a photobioreactor in according with a fifth exemplary embodiment includes three culturing bags 10-5. Each of the three culturing bags 10-5 has a cylindrical shape and is laid in parallel to a water level. Also, the three culturing bags 10-5 are vertically disposed parallel to each other. Although the number of culturing bags 10-5 is not limited, the culturing bags 10-5 should be disposed at a proper depth in consideration that sunlight required for photosynthesis of marine microalgae does not reach the culturing bags 10-5 when the culturing bags 10-5 are disposed at very deep positions.

Also, the photobioreactor includes at least one weight 60 connected to at least one culturing bag 10-5 including the lowermost culturing bag 10-5 of the culturing bags 10-5. For example, although the photobioreactor including the weight 60 connected to only the lowermost culturing bag 10-5 and the intermediate culturing bag 10-5, the present disclosure is not limited thereto. For example, the weight 60 may be connected to only the lowermost culturing bag 10-5 or the whole culturing bags 10-5. That is, although the weight (as an example) is essentially connected to the lowermost culturing bag 10-5 to maintain the entire arrangement and balance the culturing bags 10-5, the weight 60 may be selectively connected to the rest culturing bags 10-5.

Figure 6:
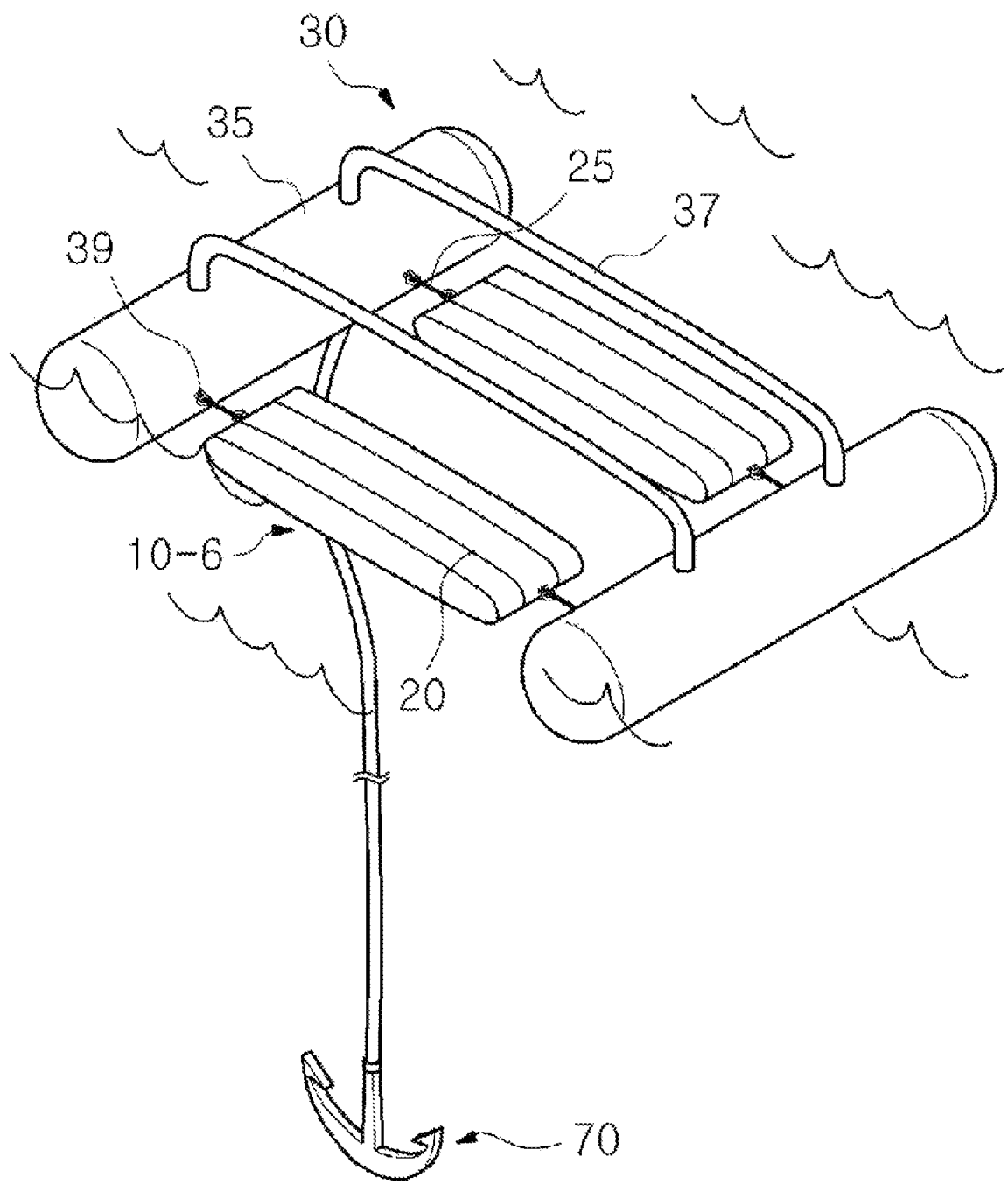
FIG. 6 is a schematic view of a photobioreactor in accordance with a sixth exemplary embodiment.

FIG. 6 is a schematic view of a photobioreactor in accordance with a sixth exemplary embodiment.

Referring to FIG. 6, a photobioreactor in accordance with a sixth exemplary embodiment includes a floating unit 30 having at least two pairs of connection points spaced a predetermined distance from each other and two culturing bags 10-6. Each of the two culturing bags 10-6 has a long length and a narrow width. Also, the two culturing bags 10-6 are respectively connected to the pair of connection points through ropes 25 connected to both ends of a length direction of each of the culturing bags 10-6.

In the current embodiment, like the foregoing embodiments, the floating unit 30 a pair of floating members 35 spaced from each other and a connection frame 37 connecting the pair of floating members 35 to each other while maintaining a predetermined distance between the floating members 35. The floating members 35 are connected to each other through connection rings 39 disposed at connection points facing each other. Here, the floating unit 30 is not limited to the above-described shape. For example, the floating unit 30 may be changed in shape and size according to those of the culturing bag 10-6.

Also, the photobioreactor in accordance with the current embodiment includes a fixing unit 30 hung at the floating unit 30. Here, a weight is not hung at the culturing bag 10-6.

As described above, since the culturing bag 10-6 has the long length and narrow width, the culturing bag 10-6 is connected to each of the connection rings 39 facing each other through the rope 25 connected to both ends of the length direction of the culturing bag 10-6, and a weight is not connected to the culturing bag 10-6, the culturing bag 106 may be freely overturned by a wave or a flow of seawater.

Since the culturing bag 10-6 is freely overturned by the wave and the flow of seawater, marine microalgae may be uniformly distributed within the culturing bag 10-6 without separately supplying gas to cause a mixing operation by bubbles. Thus, culturing environments of the marine microalgae may be excellently maintained.

Figure 7:
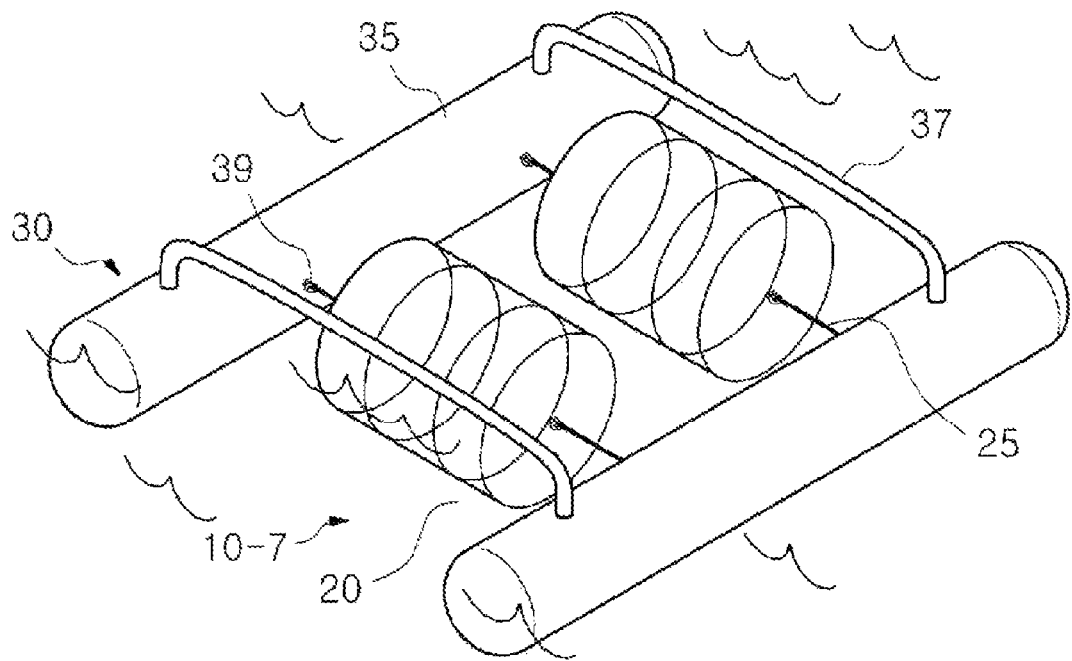
FIG. 7 is a schematic view of a photobioreactor in accordance with a seventh exemplary embodiment.

FIG. 7 is a schematic view of a photobioreactor in accordance with a seventh exemplary embodiment.

Referring to FIG. 7, a photobioreactor in accordance with a seventh exemplary embodiment includes a culturing bag 10-7 having a long cylindrical shape and is connected to a floating unit 30 in a state where it is laid in parallel to a water level. In this case, the culturing bag 10-7 may be freely overturned by a wave or a flow of seawater.

Figure 8:
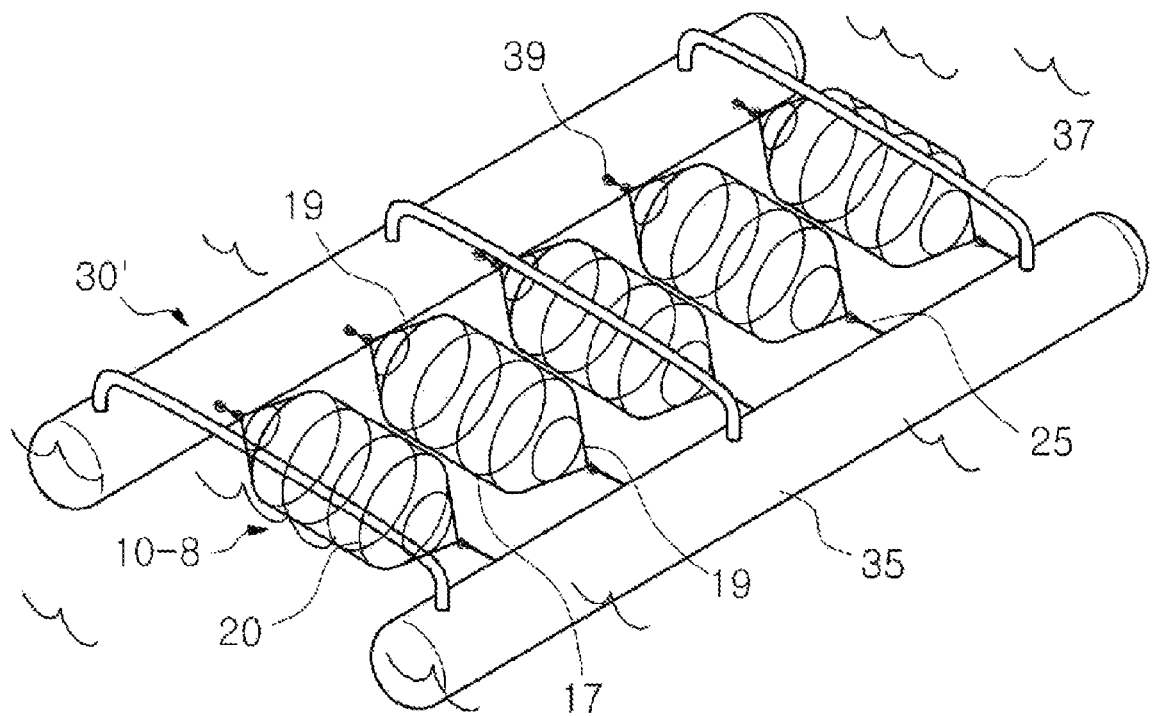
FIG. 8 is a schematic view of a photobioreactor in accordance with an eighth exemplary embodiment.

FIG. 8 is a schematic view of a photobioreactor in accordance with an eighth exemplary embodiment.

Referring to FIG. 8, a photobioreactor in accordance with an eighth exemplary embodiment includes a culturing bag 10-8 in which has a central portion having a cylindrical shape and a pair of cone-shaped portions disposed on both ends of the central portion having the cylindrical shape. Here, the culturing bag 10-8 is connected to a floating unit 30' through a rope 25 connected to an apex of each of the cone-shaped portions. In the culturing bag 10-8 in accordance with the current embodiment, the culturing bag 10-8 may be further freely overturned by a wave or a flow of seawater when compared to that in accordance with the seventh exemplary embodiment.

As shown in FIG. 8, in a photobioreactor in accordance with an eighth exemplary embodiment, the floating unit 30' may be expanded in a length direction thereof. Also, a plurality of connection rings 39 is provided to the floating unit 30'. Thus, the culturing bag 10-8 may be connected to the pair of connection rings 39 to expand a scale thereof. Although not shown, the floating unit 30' may be expanded in a width direction thereof. Thus, it is assumed that the photobioreactor may be increased in scale to increase commercial mass-culture of the marine microalgae.

As described above, the photobioreactor for mass-culturing the marine microalgae using a semi-permeable membrane in accordance with the exemplary embodiments may be utilized for mass-culturing the microalgae in following processes.

First, the photobioreactor in accordance with the exemplary embodiments may be applied for the whole microalgae which are cultured in seawater. Particularly, the photobioreactor is adopted for commercially mass-culturing the marine microalgae so as to produce bio-energy. In this case, carbon dioxide that is a main culprit of environment pollution related to global warming may be reduced in quantity. As a result, the photobioreactor may be sustainable.

Also, the nutrients contained in the seawater may be introduced through the semi-permeable membrane to remove the excreta and the metabolites disturbing the growth of the marine microalgae. Thus, since it is unnecessary to supply and replace the separate culture media, the manpower and costs of managing and operating the photobioreactor may be significantly reduced.

Also, the manufacturing costs of the photobioreactor may be significantly inexpensive when compared to those of a photobioreactor in accordance with a related art. Furthermore, the photobioreactor may utilize the wide sea as an installation place to overcome commercial and spatial restrictions which act as stumbling blocks of the scale expansion that is necessary for mass-culturing the microalgae. That is, the most important thing in the photobioreactor is to transmit optical energy. Thus, when this is considered as one of facts by which the scale expansion of the photobioreactor is difficult, the photobioreactor in accordance with the exemplary embodiments may be installed in the seawater in which a ratio of surface area per unit volume can be unlimitedly expanded to enable the volume of the photobioreactor to be easily expanded in a horizontal direction even though the photobioreactor is increase the ratio of surface area per unit volume, i.e., the scale expansion of the photobioreactor is realized.

Furthermore, since the scale of the photobioreactor may be expanded in a vertical direction, different kinds of microalgae may be cultured at the same time according to a depth of seawater. That is, the depth at which the culturing bag is disposed may be adjusted to secure conditions adequate for growing the microalgae or producing metabolites to be produced.

As described above, the photobioreactor for mass-culturing the marine microalgae using the semi-permeable membrane may affect the development of marine resources in our country because earth's surface covered by sea is so much greater than the dry land, i.e., Korea is surrounded by water on three sides. That is, the photobioreactor may have an infinite of utilities in which utilization efficiency of national land may be maximized by using wide sea than the relatively narrow national land.

As described above, since the photobioreactor for mass-culturing the marine microalgae using the semi-permeable membrane is provided, the photobioreactor may be manufactured at a low cost and free from the spatial restrictions, thereby enabling the expansion of the photobioreactor in both the horizontal and vertical directions. Furthermore, the manpower and costs for managing and operating the photobioreactor may be significantly reduced without producing, supplying, and replacing the culture media to easily and economically mass-culture the microalgae. Thus, the photobioreactor may enable the mass production of useful products including bio-energy and removes stumbling block of the commercial mass-production while mass-producing the useful products including the bio-energy.

In the photobioreactor in accordance with the exemplary embodiments, the marine microalgae may be automatically cultured without separately replacing the culture media in the seawater. Thus, the photobioreactor may be industrially utilized in various fields such as fungus bodies, functional health foods, animal feeds, removal of carbon dioxide, and production of biodiesel. In addition, the photobioreactor may be used for removing waste organic matters such as domestic wastewater, industrial wastewater, and livestock wastewater.

Although the photobioreactor for mass-culturing marine microalgae using the semi-permeable membrane has been described with reference to the specific embodiments, it is not limited thereto. Therefore, it will be readily understood by those skilled in the art that various modifications and changes can be made thereto without departing from the spirit and scope of the present invention defined by the appended claims.

What is claimed is:

1. A photobioreactor for mass-culturing marine microalgae using a semi-permeable membrane, which is installed in a floating type on a water level or soaked at a predetermined depth from the water level to mass-culture isolated marine microalgae, the photobioreactor comprising:

a culturing bag formed of the semi-permeable membrane through which enables seawater to exist, but prevents the marine microalgae from penetrating, the culturing bag being configured to provide a three-dimensionally culturing space for accommodating the marine microalgae; and a floating unit connected to the culturing bag to dispose the culturing bag near the sea level, thereby exposing the culturing bag to sunlight.

2. The photobioreactor of claim 1, further comprising a gas supply tube connected to a lower portion of the culturing bag; and a gas supply unit configured to supply external air into the culturing bag through the gas supply tube, wherein the marine microalgae is uniformly distributed within the culturing bag due to mixing operations of bubbles.

3. The photobioreactor of claim 2, wherein the culturing bag has an upper portion having a vertical cylindrical shape and a lower portion having an inverted cone shape, and the gas supply tube and the weight are connected to an apex of the lower portion having the inverted cone shape.

4. The photobioreactor of claim 3, further comprising a fixing unit fixed to a sea bottom in a state where the fixing unit is connected to one of the floating unit, the culturing bag, and the weight to restrict a moving range of the photobioreactor.

5. The photobioreactor of claim 2, further comprising a fixing unit fixed to a sea bottom in a state where the fixing unit is connected to one of the floating unit, the culturing bag, and the weight to restrict a moving range of the photobioreactor.

6. The photobioreactor of claim 2, wherein the culturing bag has one of an inverted cone shape, a flexible tune shape, and a bag shape, and the gas supply tube and the weight are connected to an apex of the culturing bag.

7. The photobioreactor of claim 6, further comprising a fixing unit fixed to a sea bottom in a state where the fixing unit is connected to one of the floating unit, the culturing bag, and the weight to restrict a moving range of the photobioreactor.

8. The photobioreactor of claim 6, wherein the culturing bag is filled with exhaust gas for supplying carbon dioxide or a waste organic matter for supplying a nitrogen source, and the exhaust gas or the water organic matters filled into the culturing bag is stored in the culturing bag by the semi-permeable membrane, but is not discharged into the sea.

9. The photobioreactor of claim 8, further comprising a fixing unit fixed to a sea bottom in a state where the fixing unit is connected to one of the floating unit, the culturing bag, and the weight to restrict a moving range of the photobioreactor.

10. The photobioreactor of claim 1, wherein the culturing bag is provided in plurality, and the plurality of culturing bags are vertically arranged, and
wherein the photobioreactor comprises at least one weight connected to one or more culturing bags comprising the lowermost culturing bag.

11. The photobioreactor of claim 1, further comprising a fixing unit fixed to a sea bottom in a state where the fixing unit is connected to one of the floating unit, the culturing bag, and a weight to restrict a moving range of the photobioreactor.

12. A photobioreactor for mass-culturing marine microalgae using a semi-permeable membrane, which is installed in a floating type on a water level or soaked at a predetermined depth from the water level to mass-culture isolated marine microalgae, the photobioreactor comprising:
a culturing bag formed of the semi-permeable membrane through which enables seawater to exist, but prevents the marine microalgae from being penetrated, the culturing bag being configured to provide a three-dimensionally culturing space for accommodating the marine microalgae; and
a floating unit connected to the culturing bag to dispose the culturing bag near the sea level, thereby exposing the culturing bag to sunlight, wherein the floating unit has at least one pair of connection points spaced a predetermined distance from each other,
the culturing bag has a long length and a narrow width and connected to the pair of connection points through one rope connected to each of both ends of a length direction of the culturing bag, and
the culturing bag is freely overturned by movement of a wave or seawater.

13. The photobioreactor of claim 12, wherein the culturing bag has a long cylindrical shape and is connected to the floating unit in a state where the culturing bag is laid in parallel to a water level.

14. The photobioreactor of claim 13, wherein the culturing bag has a central portion having a cylindrical shape and a pair of cone-shaped portions on both ends of the central portion, and the rope is connected to an apex of each of the cone-shaped portions.

15. The photobioreactor of claim 13, further comprising a fixing unit fixed to a sea bottom in a state where the fixing unit is connected to the floating unit.

16. The photobioreactor of claim 12, further comprising a fixing unit fixed to a sea bottom in a state where the fixing unit is connected to the floating unit.

* * * * *